(12) United States Patent
Hontzsch et al.

(10) Patent No.: US 7,887,540 B2
(45) Date of Patent: Feb. 15, 2011

(54) DEVICE FOR DRILLING OR FOR INSERTING IMPLANTS

(75) Inventors: Dankward Hontzsch, Tubingen (DE); Beatrice Steiner, Davos (CH); Stephan Rupp, Küblis (CH)

(73) Assignee: Synthes USA, LLC, West Chester, PA (US)

( * ) Notice: Subject to any disclaimer, the term of this patent is extended or adjusted under 35 U.S.C. 154(b) by 750 days.

(21) Appl. No.: 10/883,226

(22) Filed: Jul. 1, 2004

(65) Prior Publication Data

US 2005/0004577 A1 Jan. 6, 2005

Related U.S. Application Data

(63) Continuation of application No. PCT/CH02/00011, filed on Jan. 9, 2002.

(51) Int. Cl.
A61F 2/46 (2006.01)

(52) U.S. Cl. .......................... 606/86 R; 606/22; 606/96

(58) Field of Classification Search ............... 606/86, 606/96, 104, 97, 98, 86 R, 87, 99, 191, 192; 279/2.01–2.04; 408/56–61, 104, 115 R, 408/115 B, 72 B, 241 B, 241 G
See application file for complete search history.

(56) References Cited

U.S. PATENT DOCUMENTS

| | | | | |
|---|---|---|---|---|
| 3,918,727 | A | * | 11/1975 | Forsythe ...................... 279/50 |
| 4,140,161 | A | * | 2/1979 | Russo et al. ................... 81/451 |
| 5,445,641 | A | | 8/1995 | Frigg et al. |
| 5,482,411 | A | * | 1/1996 | McGlasson .................. 408/1 R |
| 5,851,207 | A | * | 12/1998 | Cesarone .................. 606/86 B |
| 5,954,635 | A | * | 9/1999 | Foley et al. ................. 600/114 |
| 6,033,430 | A | | 3/2000 | Bonutti |
| 6,283,966 | B1 | * | 9/2001 | Houfburg ..................... 606/61 |
| 6,520,907 | B1 | * | 2/2003 | Foley et al. ................. 600/114 |
| 6,530,929 | B1 | | 3/2003 | Justis et al. |
| 6,793,656 | B1 | | 9/2004 | Mathews |
| 6,800,084 | B2 | | 10/2004 | Davison et al. |
| 6,929,606 | B2 | | 8/2005 | Ritland et al. |
| 7,300,440 | B2 | * | 11/2007 | Zdeblick et al. ............... 606/80 |
| 2002/0161368 | A1 | | 10/2002 | Foley et al. |
| 2003/0060826 | A1 | | 3/2003 | Foley et al. |
| 2003/0073998 | A1 | | 4/2003 | Pagliuca |
| 2003/0191371 | A1 | | 10/2003 | Smith et al. |
| 2004/0138662 | A1 | | 7/2004 | Landry et al. |
| 2004/0143265 | A1 | | 7/2004 | Landry et al. |
| 2004/0147928 | A1 | | 7/2004 | Landry et al. |
| 2004/0172022 | A1 | | 9/2004 | Landry et al. |
| 2005/0033297 | A1 | | 2/2005 | Davison |
| 2005/0080418 | A1 | | 4/2005 | Simonson et al. |

FOREIGN PATENT DOCUMENTS

| | | |
|---|---|---|
| CH | 396 304 A | 7/1965 |
| JP | 09 149907 A | 6/1997 |
| WO | WO 96 20650 A | 7/1996 |
| WO | WO9620650 * | 7/1996 |

* cited by examiner

*Primary Examiner*—Eduardo C Robert
*Assistant Examiner*—Tara R Carter
(74) *Attorney, Agent, or Firm*—Fay Kaplun & Marcin, LLP

(57) ABSTRACT

An instrument for use on a body site is provided comprising a bushing having portions, a coolant source, and a bore, wherein the instrument may be used to introduce an implant, instrument, or tool to a body site. After the implant, instrument, or tool is introduced to a body site, at least one portion of the bushing may be removed. A method of use for the instrument is also provided. A kit including the instrument is further provided.

29 Claims, 5 Drawing Sheets

DEVICE FOR DRILLING OR FOR INSERTING IMPLANTS

CROSS REFERENCE TO RELATED APPLICATION

This application is a continuation of the U.S. national phase designation of co-pending international application PCT/CH02/00011 to Hontzsch et al., filed Jan. 9, 2002, the entirety of which application is hereby incorporated by reference thereto.

FIELD OF THE INVENTION

The invention relates to a device for osteosynthetic purposes, especially for drilling, cutting threads or inserting implants in a bone.

BACKGROUND OF THE INVENTION

A drill guide bushing, which can be used for osteosynthetic purposes and especially for drilling, cutting threads or inserting implants, is known from International Application No. WO 96/20650 to Frigg. This known drill guide bushing includes a bushing, the front end of which can be bought into contact with a bone and through the rear end of which an instrument or implant can be introduced. Furthermore, this known drill guide bushing, in the region of the rear end, includes a coolant connection, through which coolant can be introduced into the drill guide bushing. It is a disadvantage of this known device that, when a bone screw is inserted, it cannot be guided at the screw shaft in the borehole of the drill guide bushing, as otherwise the drill guide bushing can no longer be removed from the bone screw because the head of the bone screw is larger in diameter.

SUMMARY OF THE INVENTION

The invention provides a remedy to this problem. It is an object of the invention to create a device, with which even a screw with a head having a diameter larger than that of the shaft, can be introduced into the cavity and the device can be removed from the implant after the screw has been screwed in.

The inventive device comprises essentially a drill guide bushing, which is divided over the whole of its length L parallel to the longitudinal axis and has a cavity and a coolant connection, which is connected with the cavity. Due to the divided construction of the drill guide bushing, it can be achieved that after a screw is brought through the cavity to the front end of the drill guide bushing and screwed in, the shells of the divided drill guide bushing can be shifted relative to one another transversely to the longitudinal axis. With that, the cavity of the drill guide bushing can be opened and the drill guide bushing can be pulled away over the head of the screw, which is larger in diameter.

In a preferred embodiment of the inventive device, the cavity tapers towards the front end of the drill guide bushing, so that the shaft of an inserted screw may be passed through the cavity wall at the front end of the drill guide bushing. The cavity may, for example, be tapered conically.

The drill guide bushing can be divided into two half shells, the contacting surfaces of which lie in planes which are parallel to one another and to the longitudinal axis. In an alternative embodiment of the inventive device, the contacting surfaces of the two half shells are tiered, the contacting surfaces of the first-half shell having elevations and the contacting surfaces of the second half shell having depressions, which are complementary to the elevations. Due to the elevations and depressions, which are disposed axially so that they engage one another when the drill guide bushing is closed, the leakproofness of the drill guide bushing can be increased, and the stability, which prevents displacement of the half shells relative to one another and parallel to the contacting surfaces, can also be increased.

Furthermore, in another alternative embodiment, the inventive device includes a holding grip, which may be fork-shaped with two rods. At one end of the holding grip, the two rods are connected with one another and, at the other end of the holding grip, each rod is connected with a different half shell of the drill guide bushing. Due to this configuration of the holding grip, the half shells can be moved relative to one another, so that the drill guide bushing can be opened or closed.

In another alternative embodiment, the inventive device includes an inner drill guide bushing, which can be introduced into the cavity. The central borehole of the inner drill guide bushing is configured so that a drill can be centered and guided, and after the inner drill guide bushing has been removed, thread-cutting tools can be passed through the cavity.

In a further alternative embodiment, the inventive device includes a trocar for centering the drill guide bushing in a plate borehole, for example, at a bone plate. The diameter of the trocar may be such that the trocar, when the inner drill guide bushing is removed, can be passed through the cavity wall of the drill guide bushing. The diameter of the trocar may also be such that the trocar can be introduced directly into the central borehole of the inner drill guide bushing. This particular configuration of the trocar, may eliminate the need to exchange the inserts when, for example, a bone screw is implanted. After the drill guide bushing is centered by means of the trocar, the latter can be pulled out of the central borehole of the inner drill guide bushing and the drill can be introduced into the central borehole. After the drilling process is concluded, the inner drill guide bushing can be removed from the cavity of the drill guide bushing and the thread-cutting tool can be inserted into the cavity of the drill guide bushing.

It may be preferable that the front end of the drill guide bushing is configured so that the drill guide bushing is tapered at the front end. This tapering may be configured conically or rounded-off and enables the front end of the drill guide bushing to be centered in a borehole or the screw heads to be countersunk, for example, in a bone plate more easily.

The inventive device therefore has the following advantages: during the surgical intervention, the drill guide bushing can be centered, for example, in a screw hole of a bone plate, so that it is prevented from slipping to the side during the intervention; a trocar can be introduced into the cavity of the drill guide bushing; a length measurement can be carried out through the drill guide bushing; the inner drill guide bushing or the trocar protrude at the front end of the drill guide bushing, so that a plate hole can be identified by touch; and a screw is trapped in the cavity until the two half shells of the drill guide bushing are opened.

BRIEF DESCRIPTION OF THE DRAWINGS

The invention and further developments of the invention are explained in greater detail in the following by means of partially diagrammatic representations of several examples. In the drawings.

DETAILED DESCRIPTION OF THE INVENTION

Figure 1:
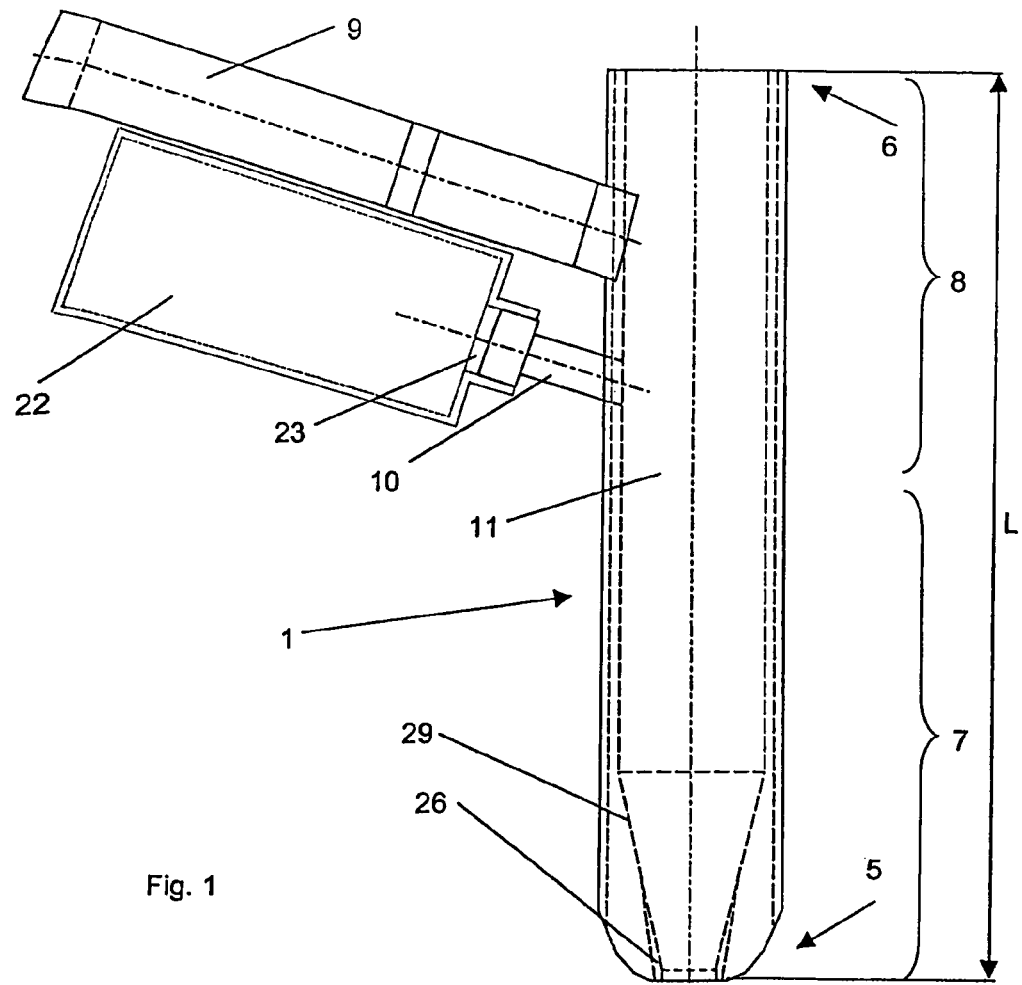
FIG. 1 shows a side view of an embodiment of the inventive device.
Figure 2:
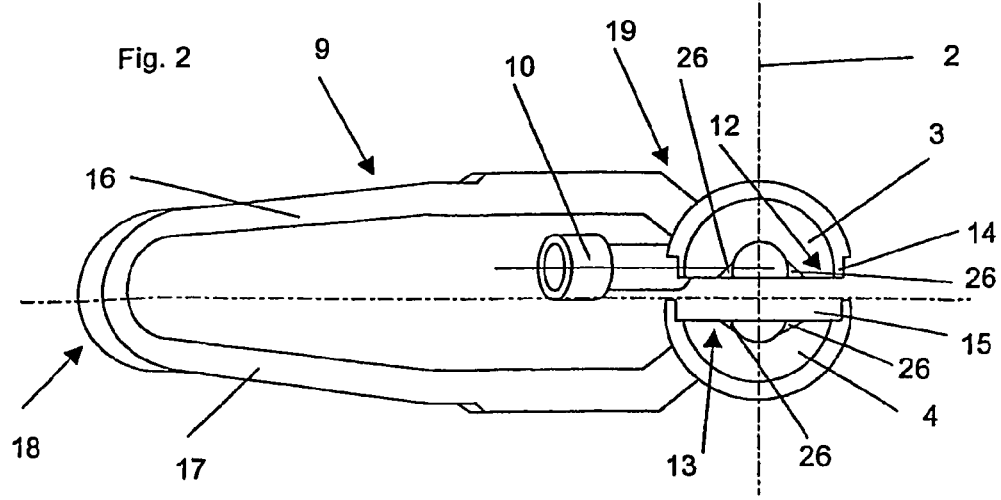
FIG. 2 shows a plan view of the embodiment of FIG. 1.

FIGS. 1 and 2 show the inventive device as a drill guide bushing 1, which is divided over its whole length L, with two half shells 3, 4, the contacting surfaces 12, 13 of which, extending parallel to the longitudinal axis 2, can be inserted in one another. An instrument or an implant can be inserted coaxially with the longitudinal axis 2 into the cavity 11 from the rear end 6 of the drill guide bushing 1. The cavity 11 is also open at the front end 5 of the drill guide bushing 1, so that when the front end 5 of the drill guide bushing 1 is placed against a bone or an implant, the drill guide bushing 1 can be used to guide a drill or another instrument axially displaceably in the cavity 11. A holding grip 9 and a coolant connection 10 are mounted at the rear segment 8, which adjoins the rear end 6 of the drill guide bushing 1. A coolant can be passed through the coolant connection 10 directly into the cavity 11 in the drill guide bushing 1, so that a drill, for example, can be cooled. The contacting surfaces 12 of the first half shell 3 have elevations 14, which are parallel to the longitudinal axis 2 and can be inserted into the complementary depressions in the contacting surfaces 13 of the second half shell 4. The fork-shaped holding grip 9 comprises two rods 16, 17, which are connected with one another at the first end 18 of the holding grip 9, and connected with a half shell 3, 4 at the second end 19 of the holding grip 9. The half shells 3, 4 may be removed from one another by pushing the rods 16, 17 apart and the drill guide bushing 1 is divided parallel to the longitudinal axis 2. On the other hand, when the rods 16, 17 are pushed together, the half shells 3, 4 can be joined together at their contacting surfaces 12, 13, so that the drill guide bushing 1 is closed. In the embodiment shown here, the front end 5 of the drill guide bushing 1 is constructed so that the front end 5 of the drill guide bushing 1 can be inserted into a depression of an implant (not shown), which is used to accommodate the screw head of a bone screw. This can ensure an accurate fit, whereby the centering of the drill guide bushing 1 can be attained via the depression in a bone plate. The cavity 11 is tapered towards the front end 5 by a cone 29 in the front segment 7 of the drill guide bushing 1. Because the cavity 11 tapers towards the front end 5 of the drill guide bushing 1 and because of the convex configuration of the front end 5 on the outside at the drill guide bushing 1, the compressed half shells 3, 4 are not jammed between the depression in the plate and the bone screw as the latter is screwed in. In the embodiment of the inventive device shown here, three cones are mounted at the front end 5 of the drill guide bushing 1. They adjoin one another axially, are coaxial with the longitudinal axis 2, and due to their different conical angles, provide a convex configuration of the front end 5 of the drill guide bushing 1. These cones are suitable for centering the front end 5 of the drill guide bushing 1 in a depression for accommodating a screw head at a bone plate. Due to this configuration of the front end 5 of the drill guide bushing 1, the latter does not slip out of the depression for the screw head if, for example, the two half shells 3, 4 are separated slightly during the determination of the screw length, so that the centering of the front end 5 is maintained.

The drill can be cooled during the drilling process. This is facilitated by a coolant container 22, the opening 23 of which can be connected to the coolant connection 10 at the drill guide bushing 1. The length of the bone screw, protruding over the plate, can be determined through the cavity 11. For screwing the bone screw in completely, the two half shells 3, 4 are separated, so that the screw head at the front end 5 of the drill guide bushing 1 fits through the tapered cavity 11. As long as the screw is not screwed through the opened front end 5 of the drill guide bushing 1, the latter can be taken out once again with the drill guide bushing 1 closed without the possibility of losing the screw in the soft parts. Two grooves 26 are provided at the front end 5 of the drill guide bushing 1 in the cavity 11 of the drill guide bushing 1. When viewed parallel to the contacting surfaces 12, 13 and perpendicularly to the longitudinal axis 2 of the drill guide bushing 1, these grooves 26 extend parallel to the contacting surfaces 12, 13 and are divided symmetrically in their length by the contacting surfaces 12, 13. Viewed perpendicularly to the contacting surfaces 12, 13, the grooves 26 extend at an angle to the longitudinal axis 2, this angle being smaller than half the conical angle of the cone 29, so that the depth of the grooves 26 decreases from the front end 5 in the direction of the rear end 6 of the drill guide bushing 1 and the grooves 26 taper off in the cone 29. Because of these two grooves 26, the half shells 3, 4 need only be separated slightly for determining, for example, the screw length. For this reason, the front end 5 of the drill guide bushing 1 is less likely to slip out of the depression of the plate hole and that subsequently the depression can be found only with difficulty, if at all, due to the soft parts.

Figure 3:
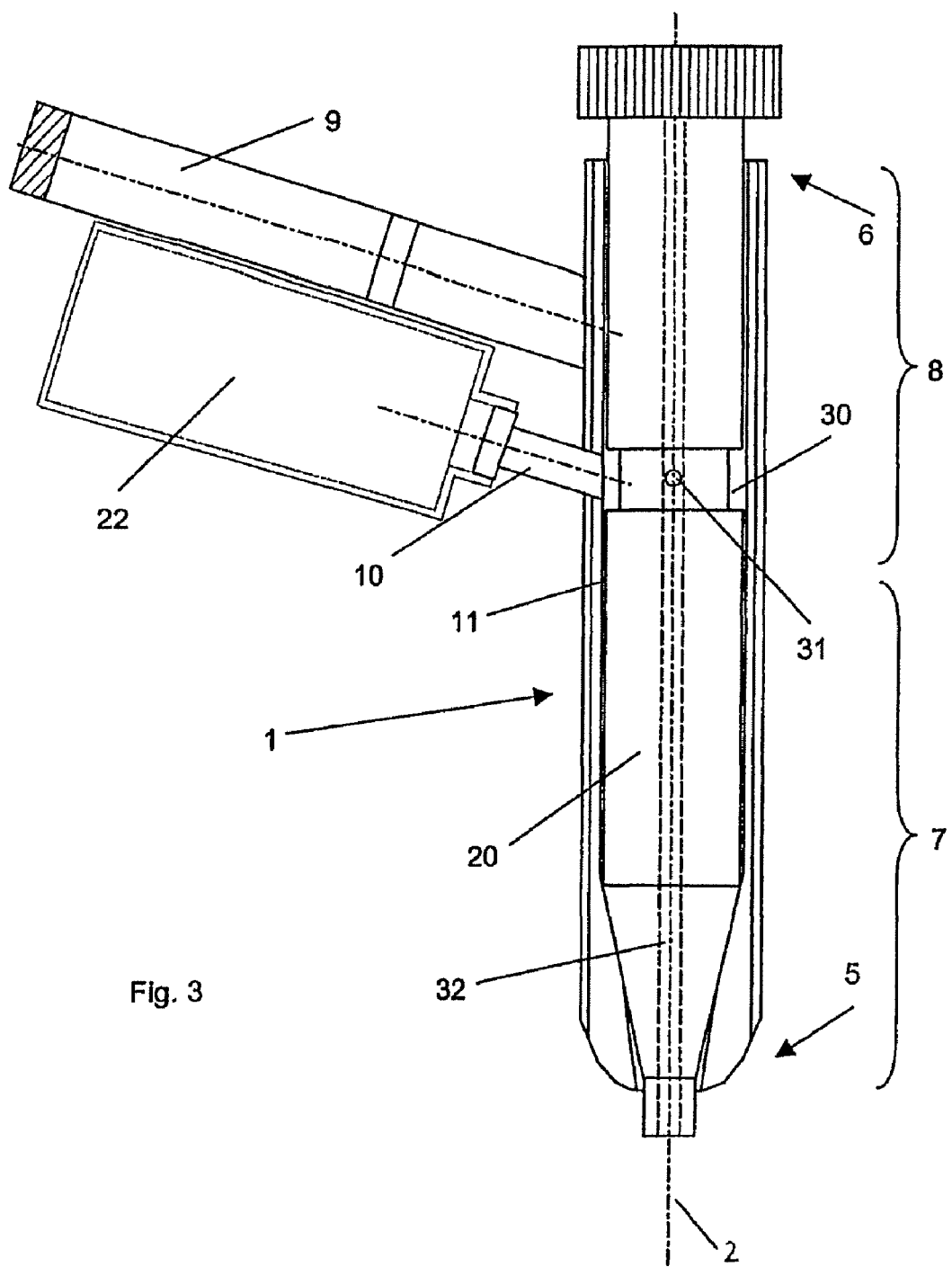
FIG. 3 shows a cross-sectional side view of an alternative embodiment of the inventive device together with an inner drill guide bushing.
Figure 4:
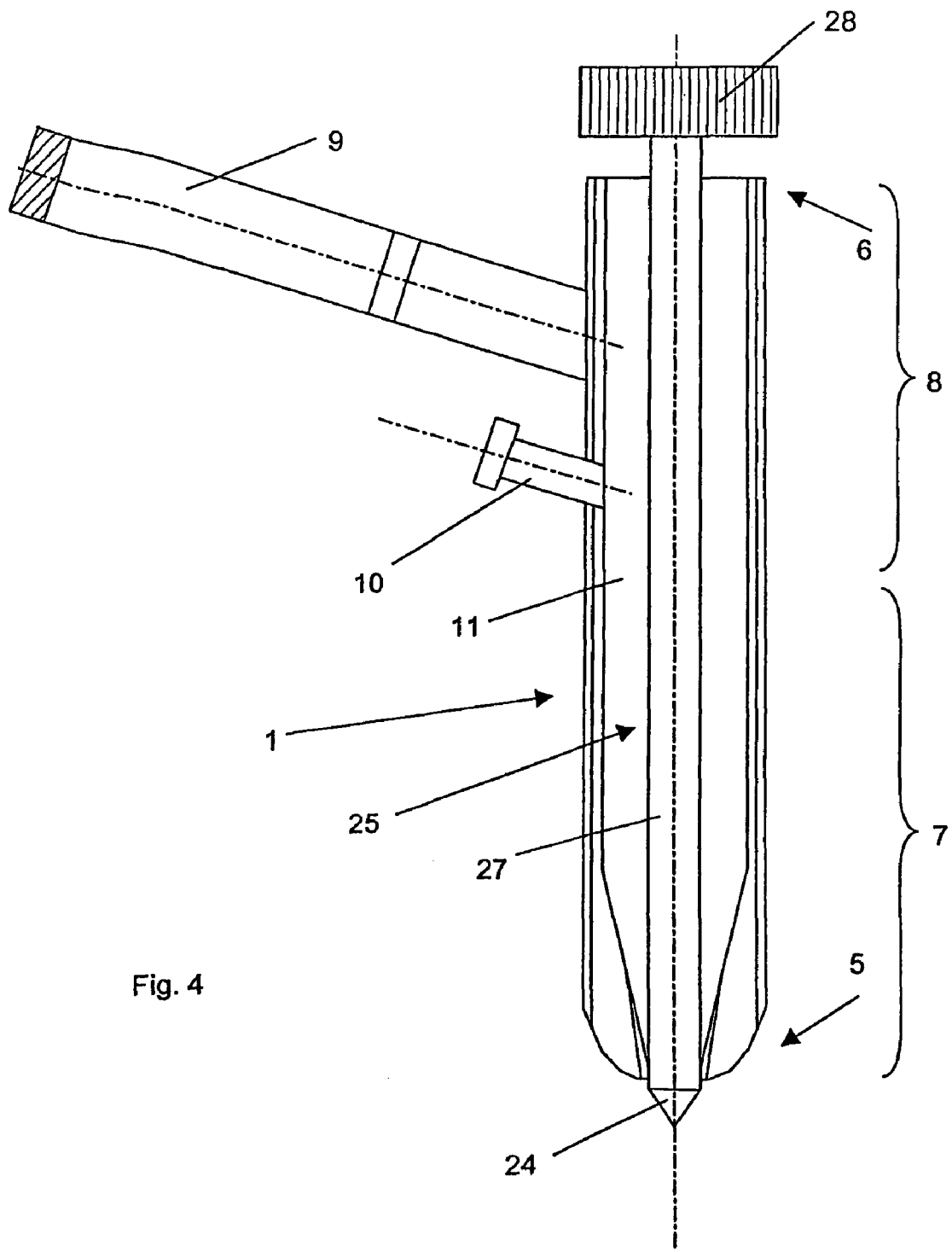
FIG. 4 shows a cross-sectional side view of an alternative embodiment of the inventive device together with a trocar.

FIG. 3 shows the device of FIG. 1 with a hollow cylindrical inner drill guide bushing 20. The inner drill guide bushing 20 can be inserted coaxially with the longitudinal axis 2 from the rear end 6 of the drill guide bushing 1 into the cavity 11. In the inserted state, the inner drill bushing 20 protrudes beyond the front end 5 of the drill guide bushing 1. During the drilling process, the inner drill guide bushing 20 is inserted into the two-part drill guide bushing 1. While drilling, coolant can be injected from the coolant container 22 into the drill guide bushing 1. The coolant is pressed through an annular groove 30, which is mounted level with the coolant connection 10 at the outside of the inner drill guide bushing 20, and enters the inner drill guide bushing 20 through boreholes 31, which are disposed radially with respect to the longitudinal axis 2 in the annular groove 30 and extend into the central boreholes 32 of the inner drill guide bushing 20. The coolant passes through the central boreholes 32 along the drill to the front end 5 of the drill guide bushing 1 and to the tip of the drill, FIG. 4 shows the inventive device with a drill guide bushing 1, as shown in FIG. 1, together with a trocar 25. The trocar 25 includes a cylindrical shaft 27 with a tip 24 at its front end and a holding grip 28 at its rear end. For centering the drill guide bushing 1, the trocar 25 is introduced from the rear end 6 of the drill guide bushing 1 into the cavity 11 until the tip 24 of the trocar 25 protrudes beyond the front end 5 of the drill guide bushing 1.

During the surgical procedure, the drill guide bushing 1 is guided by a stab incision through the soft parts onto the plate 5 (not shown), which has been pushed underneath. The drill guide bushing 1 and the trocar 25 can be guided selectively to the plate hole with the tip 24 of the trocar 25, which protrudes over the front end of the drill guide bushing 1. After the plate hole has been found, the drill guide bushing 1 is introduced with its front end 5 into the depression at the plate hole and is centered by the latter. For the embodiment of the drill guide bushing 1 and the trocar 25 shown here, the trocar 25 is removed from the drill guide bushing 1 after the latter is centered in the depression at the plate hole and the inner drill guide bushing 20 is introduced, so that the drill can be introduced into the central borehole 32 of the inner drill guide bushing 20 and the hole can be drilled. Subsequently, the inner drill guide bushing 20 is removed from the cavity 11 in the drill guide bushing 1 and the thread is cut through the cavity 11 in the drill guide bushing 1.

Figure 5:
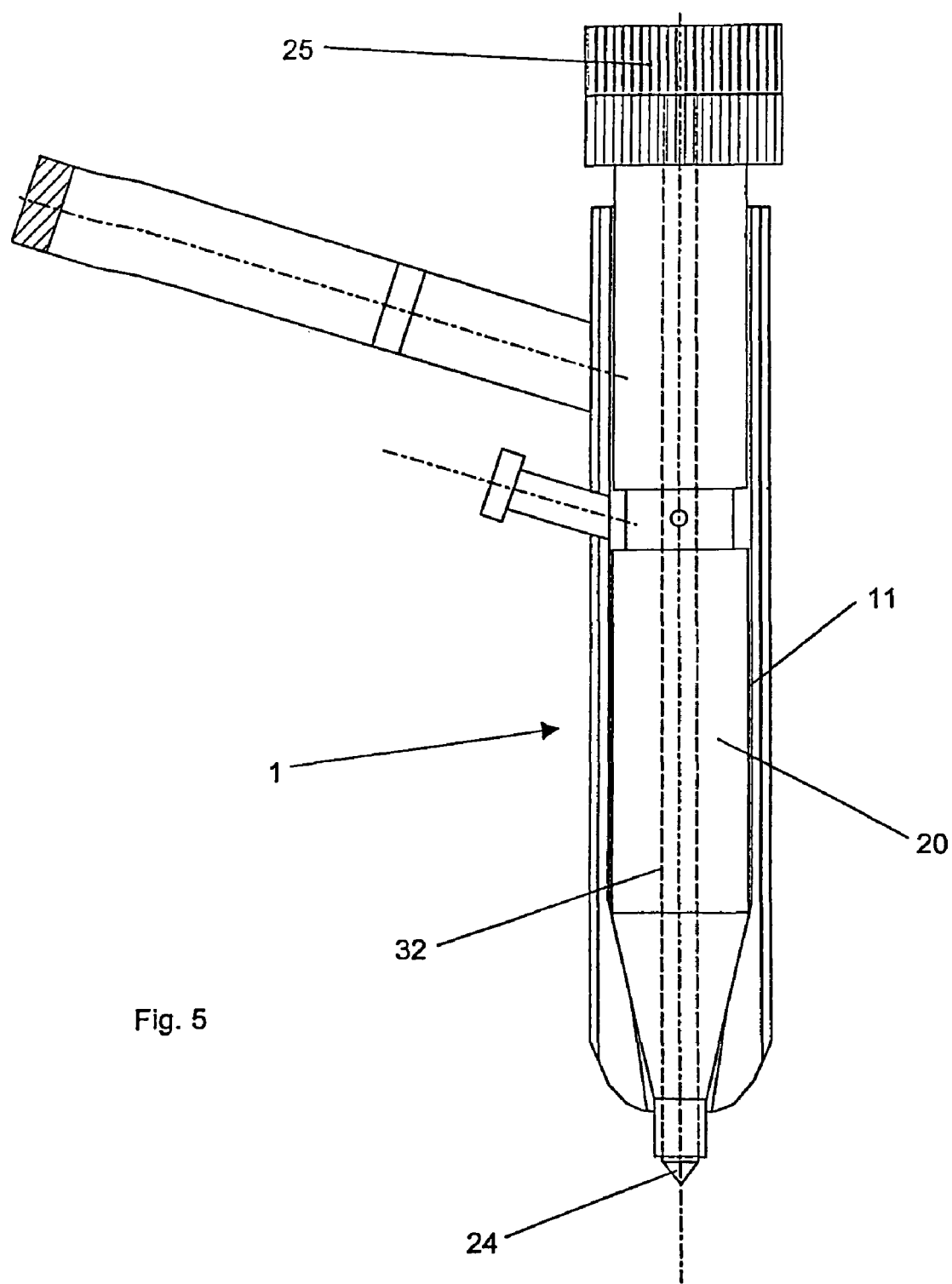
FIG. 5 shows the device of FIG. 3, into which a trocar has been inserted.

A different embodiment of the inventive device is shown in FIG. 5. The possibility exists here of introducing the trocar 25 into the central borehole 32 of the inner drill guide bushing 20, so that the tip 24 of the trocar 25 protrudes from the central borehole 32 at the front end 5 of the drill guide bushing 1 and protrudes beyond the front end 5. It can therefore be achieved that after the device is centered, only the trocar 25 has to be pulled out of the central borehole 32 of the inner drill guide bushing 20, after which the drill can be introduced into the central borehole 32 and the hole can be drilled. Subsequently, the inner drill guide bushing 20 is removed from the cavity 11 of the drill guide bushing 1 and the thread is cut.

Figure 6:
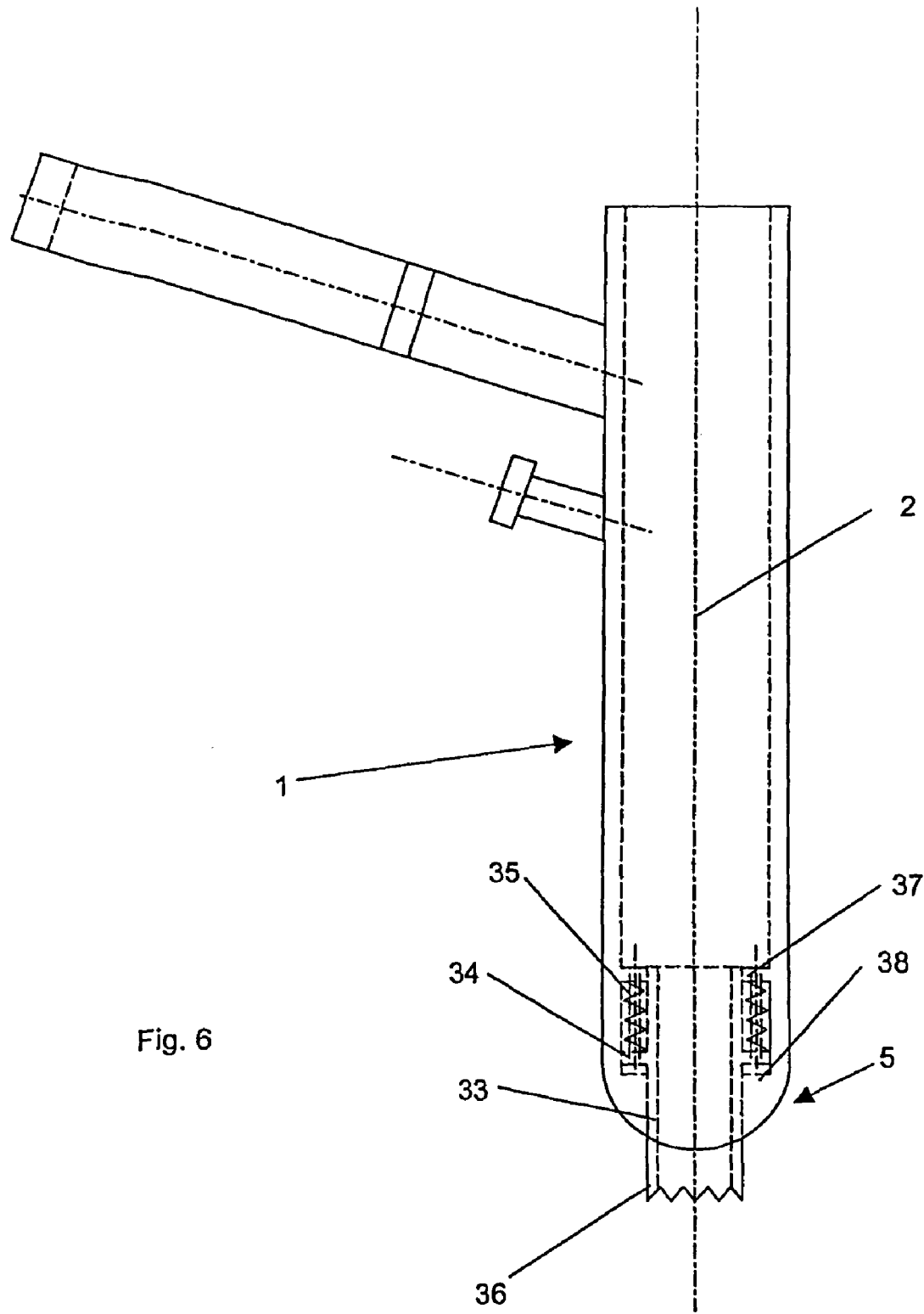
FIG. 6 shows a cross-sectional side view of an alternative embodiment of the inventive device with an insert at the front end.

A further embodiment is shown in FIG. 6. An insert 33, which can be shifted coaxially to the longitudinal axis 2, is disposed at the front end 5 of the 2-part drill guide bushing 1. The insert 33 is in the form of a sleeve and includes a concentric collar 34. The axial displaceability of the insert 33 is limited owing to the fact that the collar 34 can be moved axially in the drill guide bushing 1 only between a rear stop 37 and a front stop 38. Springs 35, by means of which the insert 33 is pressed against the front end 5 of the drill guide bushing 1, are disposed between the rear stop 37 and the collar 34 parallel to the longitudinal axis 2. Furthermore, the front end 36 of the insert 33 is serrated.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed:

1. An instrument for use on a body site comprising:
    a guide having a proximal end, a distal end, a bore therethrough, a longitudinal axis, and a length along the longitudinal axis;
    wherein the bore is sized and configured to receive an implant, instrument, or tool;
    wherein the bore is connected to a coolant source; and
    a handle including a plurality of handle members with first and second ends, wherein the first ends of the plurality of handle members are connected, and the second ends of the plurality of handle members are connected to a plurality of tips, the first ends facing a first direction and the second ends facing a second direction that is opposite the first direction, wherein the first ends are a proximal-most end of each of the plurality of handle members and the second ends are a distal-most end of each of the plurality of handle members;
    wherein the guide includes the plurality of tips, at least one of the tips is moveable with respect to the other of said tips, said movement being substantially transverse to the longitudinal axis of the guide, said transverse movement being caused by the introduction of the implant, instrument, or tool.

2. The instrument of claim 1, wherein the bore tapers toward the distal end.

3. The instrument of claim 2, wherein the implant, instrument, or tool is a screw having a head.

4. The instrument of claim 3, the bore further comprising a diameter at the distal end, the head further comprising a diameter, wherein the diameter of the head is larger then the diameter of the bore at the distal end, prior to the introduction of the screw.

5. The instrument of claim 1, wherein each top remains moveable after the introduction of the implant, instrument, or tool.

6. The instrument of claim 1, the tips further comprising side surfaces, wherein the side surfaces of each tip have elevations corresponding to depressions in an adjacent tip.

7. The instrument of claim 1, wherein the plurality of handle members are a first handle member and a second handle member, and
    wherein the plurality of tips are a first tip and a second tip, and the second ends of the first and second handle members are coupled to the first and second tips, respectively.

8. The instrument of claim 7, wherein the first and the second handle members are rods that are substantially parallel to one another.

9. A method of inserting an object into a body site comprising the steps of:
    (a) providing an instrument having a guide and a handle, the guide having a proximal end, a distal end, a bore therethrough, a longitudinal axis, and a length along the longitudinal axis, the guide is comprised of a plurality of tips, at least one of the tips is moveable with respect to the other of said tips, transverse to the longitudinal axis of the guide as a result of the introduction of the object into the body site, the tips remaining moveable with respect to one another after the introduction of the object into the body site; and
    wherein the handle comprises a plurality of handle members with first and second ends, wherein the first ends of the plurality of handle members are connected, and the second ends of the plurality of handle members are connected to the plurality of tips, the first ends facing a first direction and the second ends facing a second direction that is opposite the first direction, and wherein the first ends are a proximal-most end of each of the plurality of handle members and the second ends are a distal-most end of each of the plurality of handle members;
    (b) inserting the object into the proximal end;
    (c) introducing the object into the body site to a depth where at least a portion of the object remains in the bore;

(d) moving at least one tip of the guide with respect to the other of said tips of the guide to that the portion of the object remaining in the bore is at least partially accessible from outside the bore.

10. The method of claim 9, further comprising the step of moving all of the tops of the guide transversely away from the object remaining in the bore so that the object is at least partially accessible from outside the bore.

11. The method of claim 9, wherein the object is a screw having a head.

12. The method of claim 11, the bore further comprising a diameter at the distal end, the head further comprising a diameter, wherein the diameter of the head is larger than the diameter of the bore at the distal end, prior to the introduction of the screw.

13. The method of claim 9, wherein the bore tapers toward the distal end.

14. The method of claim 9, wherein the plurality of handle members are a first handle member and a second handle member,
wherein the plurality of tips are a first tip and a second tip, and the second ends of the first and second handle members are coupled to the first and second tips, respectively.

15. The method of claim 14, wherein the first and the second handle members are rods that are substantially parallel to one another.

16. The method of claim 9, the bore further comprising a connection to a coolant source.

17. The method of claim 16, further comprising the step of introducing a coolant into the bore during steps (b) or (c).

18. The method of claim 9, wherein the object is an implant.

19. The method of claim 9, wherein the object is an instrument.

20. A kit for use with inserting an object into a body site comprising:
(a) an instrument having a guide and a handle, the guide having a proximal end sized and configured to receive the object, a distal end sized and configured to be placed at or near the body site, a bore extending from said proximal end to said distal end, a longitudinal axis, and a length along the a longitudinal axis, the guide further including a plurality of tips, at least one of the tips being moveable with respect to the other of said tips, said movement being substantially transverse to the longitudinal axis as a result of the introduction of the object into the body site, the tips remaining moveable with respect to one another after the introduction of the object into the body site; and wherein the handle comprises a plurality of handle members with first and second ends, wherein the first ends of the plurality of handle members are connected, and each of the second ends of the plurality of handle members are connected to a corresponding one of the plurality of tips, the first ends facing a first direction and the second ends facing a second direction that is opposite the first direction, wherein the first ends are a proximal-most end of each of the plurality of handle members and the second ends are a distal-most end of each of the plurality of handle members;
(b) a plurality of engageable tips for combination and use with the instrument.

21. An instrument for use in a patient's body, the instrument comprising:
a guide assembly having a proximal end, a distal end, a bore extending from said proximal end to said distal end, and a longitudinal axis, the guide assembly being sized and configured so that said proximal end is located outside the patient's body when the distal end is located within the patient's body, the bore being sized and configured to receive a bone affixation element, the bone affixation element having a head region and a shank region, the distal end of the guide assembly including a plurality of shells, at least one of the shells being moveable from a first position to a second position, said movement being substantially transverse to the longitudinal axis;
wherein the handle comprises a plurality of handle members with first and second ends, wherein the first ends of the plurality of handle members are connected, and the second ends of the plurality of handle members are connected to the plurality of shells, the first ends facing a first direction and the second ends facing a second direction that is opposite the first direction, wherein the first ends are a proximal-most end of each of the plurality of handle members and the second ends are a distal-most end of each of the plurality of handle members;
wherein the head region of said bone affixation element is prevented from passing completely through the distal end of the guide assembly when said plurality of shells of said guide assembly are in said first position; and
wherein the head region of said bone affixation element is capable of passing completely through the distal end of the guide assembly when said plurality of shells of said guide assembly are in said second position.

22. The instrument of claim 21, wherein the plurality of shells are biased towards the first position and wherein upon an application of force the plurality of shells are moved from the first position to the second position.

23. The instrument of claim 22, wherein the plurality of shells are a first half shell and a second half shell, the first and second half shells having contacting surfaces, the contacting surface of the first half shell including a projection and the contacting surface of the second half shell including a depression, the depression being sized and configured to receive the projection.

24. The instrument of claim 23, wherein the plurality of handle members are a first handle member, and a second handle member the second end of the first and second handle members being connected to the first and second half shell, respectively.

25. The instrument of claim 24, wherein the first half shell and the second half shell are moved into the first position by moving the first handle member and the second handle member together, and the first half shell and the second half shell are moved into the second position by moving the first rod and the second rod apart.

26. The instrument of claim 23, wherein the first and the second handle members are rods that extend substantially parallel to one another.

27. The instrument of claim 22, wherein the bore tapers toward the distal end.

28. The instrument of claim 22, the bore further including a diameter at the distal end, the head region further including a diameter, wherein the diameter of the head region is larger then the diameter of the diameter of the bore at the distal end when the plurality of shells are in the first position.

29. The instrument of claim 21, wherein the bore is connected to a coolant source.

* * * * *